US00PP36797P2

(12) United States Plant Patent
Bak

(10) Patent No.: US PP36,797 P2
(45) Date of Patent: Jul. 1, 2025

(54) ***SCHEFFLERA* PLANT NAMED 'Mato'**

(50) Latin Name: *Schefflera schizophylla*
Varietal Denomination: Mato

(71) Applicant: Corn Bak BV, Assendelft (NL)

(72) Inventor: Elly Bak, Assendelft (NL)

(73) Assignee: Corn Bak B.V. (NL)

( * ) Notice: Subject to any disclaimer, the term of this patent is extended or adjusted under 35 U.S.C. 154(b) by 0 days.

(21) Appl. No.: 18/911,567

(22) Filed: Oct. 10, 2024

(51) Int. Cl.
*A01H 5/12* (2018.01)
*A01H 6/10* (2018.01)

(52) U.S. Cl.
USPC ..... Plt./377

(58) Field of Classification Search
USPC ..... Plt./377
See application file for complete search history.

*Primary Examiner* — Susan McCormick Ewoldt
(74) *Attorney, Agent, or Firm* — Cassandra Bright

(57) ABSTRACT

A new and distinct cultivar of *Schefflera* plant named 'Mato' is disclosed, characterized by a compact growth habit, and palmately compound leaves. Plants grow rapidly and are suitable for commercial production in 13 cm and larger pots. The new variety is a *Schefflera*, typically produced as an ornamental plant.

3 Drawing Sheets

Latin name of the genus and species: *Schefflera schizophylla.*

Variety denomination: 'Mato'.

BACKGROUND OF THE INVENTION

The present invention relates to a new and distinct cultivar of *Schefflera* plant, botanically known as *Schefflera*, of the family Araliaceae, and hereafter referred to as 'Mato'.

The new *Schefflera* 'Mato' originated as a naturally induced whole plant mutation from an unnamed selection of *Schefflera schizophylla*. The new *Schefflera* was discovered and selected by the inventor in 2018 as a single plant in a controlled environment commercial greenhouse in Assendelft, the Netherlands.

Asexual reproduction of the new cultivar 'Mato' was first performed by vegetative cuttings beginning in 2018 in Assendelft, the Netherlands. The new cultivar reproduces true to type by asexual methods.

SUMMARY OF THE INVENTION

The following traits have been repeatedly observed and are determined to be the unique characteristics of 'Mato', which in combination distinguish 'Mato' as a new and distinct *Schefflera* cultivar:

1. Upright plant habit.
2. Rapid growth rate.
3. Palmately compound leaves.

PARENT COMPARISON

Plants of the new cultivar *Schefflera schizophylla* 'Mato' are similar to the parent variety in most horticultural characteristics. The new cultivar exhibits the following differences from the parent plant:

1. *Schefflera* 'Mato' has a more compact growth habit than the parent plant.

2. Foliage of *Schefflera* 'Mato' is darker green than foliage of the parent plant.

COMMERCIAL COMPARISONS

The new cultivar 'Mato' is comparable to plants of the species *Schefflera actinophylla* in many horticultural characteristics. The new cultivar, however, differs in the following:

1. Plants of 'Mato' have palmately compound leaves whereas plants of *Schefflera actinophylla* have oblanceolate leaves.

BRIEF DESCRIPTION OF THE PHOTOGRAPHS

The accompanying photograph illustrates the overall appearance of the new *Schefflera* cultivar 'Mato' showing the colors as true as is reasonably possible with colored reproductions of this type. Colors in the photograph may differ slightly from the color values cited in the detailed botanical description which accurately describes the color of 'Mato'.

Figure 1:
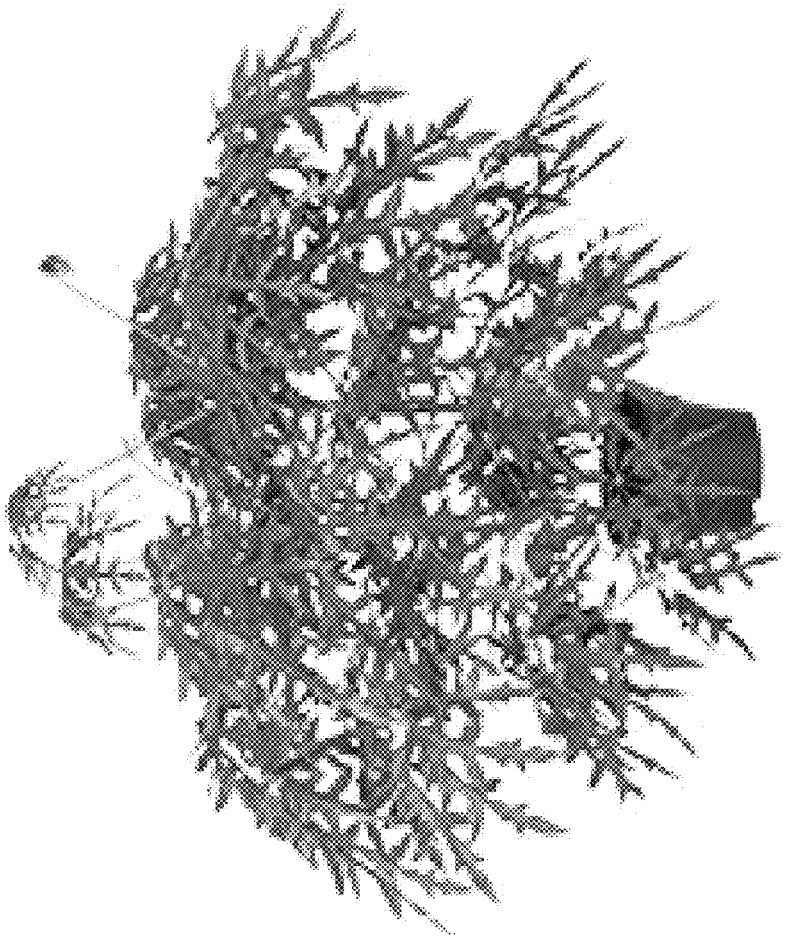

FIG. 1. shows a side view perspective of a typical potted plant of 'Mato' in a 21 cm pot.

Figure 2:
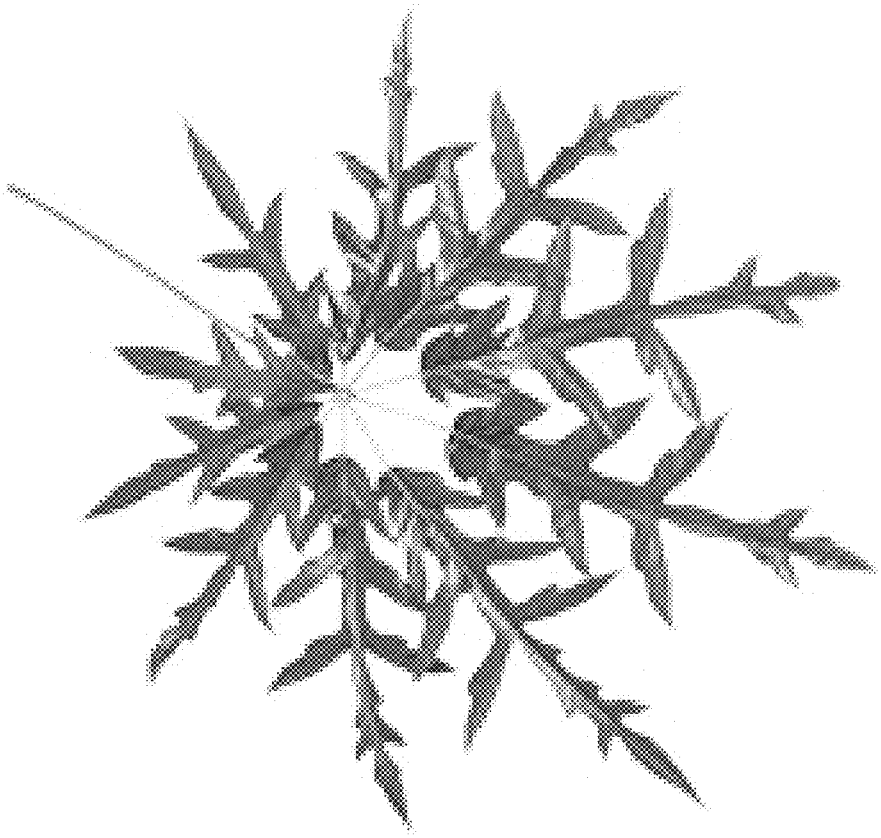

FIG. 2. shows a close up of a typical leaf of 'Mato'.

Figure 3:
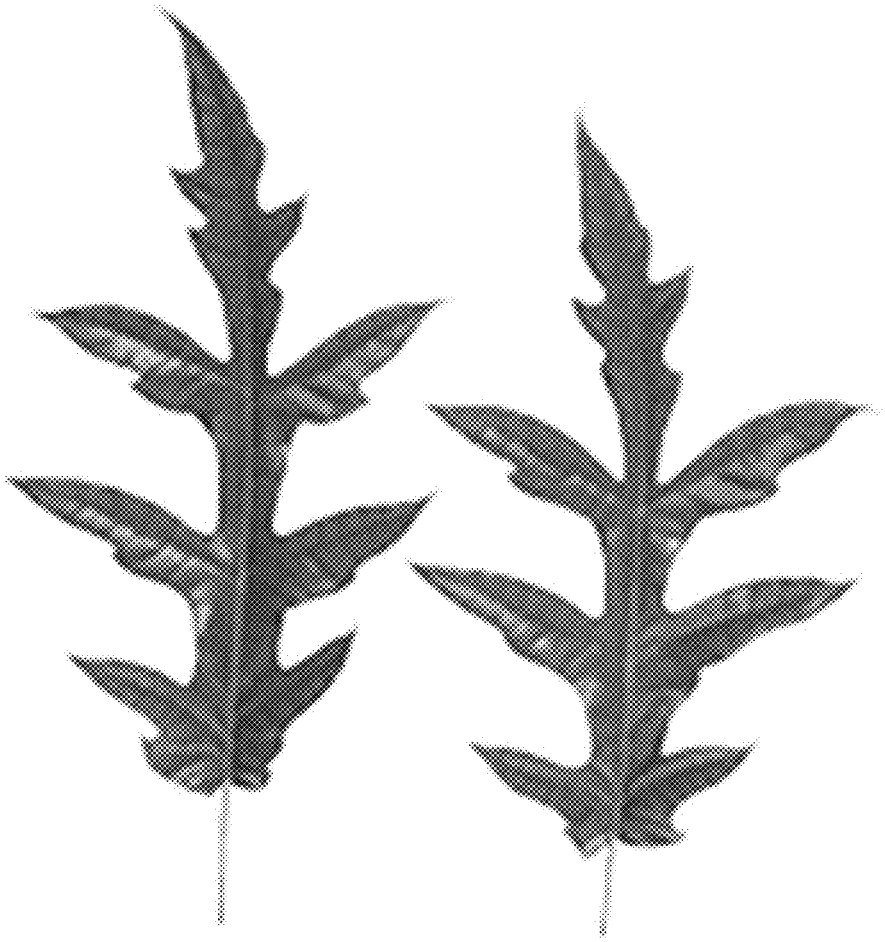

FIG. 3. shows a close up of the leaflets of 'Mato'.

DETAILED BOTANICAL DESCRIPTION

'MATO' has not been tested and observed under all possible environmental conditions. The phenotype of the new cultivar may vary with variations in environment such as temperature, light intensity, frequency of fertilization, composition of fertilizer, flowering treatment, day length and humidity, without any change in the genotype of the plant. For example, substantial differences in plant height and diameter, number of leaves, can result depending on the size of the plant at the time that flowering is induced by flowering treatment. Since treatment to induce flowering disrupts normal watering and fertilization regimens, flowering treatment of relatively smaller plants adversely affects the growth of the plant.

The aforementioned photograph, together with the following observations, measurements and values describe the new *Schefflera* 'Mato' as grown in a greenhouse in Assendelft, The Netherlands, under conditions which closely approximate those generally used in commercial practice. Plants of 'Mato' were grown in a greenhouse with day temperatures ranging from 20° C. to 28° C. and night temperatures ranging from 18° C. to 23° C. No artificial lighting or photoperiodic treatments were conducted, but plants of 'MATO' are forced into flowering. The following fertilizer is added when growing plants of 'MATO': 1 part nitrogen, 0.6 parts phosphor, 2 parts Kalium and 0.1 parts magnesium.

Color references are made to The Royal Horticultural Society Colour Chart (R.H.S.), 2001 edition, except where general colors of ordinary significance are used. Color values were taken under daylight conditions in a greenhouse in Assendelft, The Netherlands.

Botanical classification: *Schefflera schizophylla* 'MATO'.

PROPAGATION

Propagation method: Vegetative cuttings

PLANT

General appearance and form:

*Shape*.—Upright and outward, forming an overall globular shape.

*Height*.—About 50 cm to 150 cm.

*Width*.—About 2 meters.

Typical commercial pot sizes: 13 cm and larger.

Plant vigor: Good.

Growth rate: Rapid

Cold tolerance: Frost tender. Temperatures below 0° C. may damage plants.

Stem:

*Average length*.—Variable, depending up culture. 4 to 10 cm.

*Average width*.—2.5 cm.

*Shape*.—Near RHS Grey-Brown 199D.

*Texture*.—Smooth.

*Axillary buds*.—Present. Length: About 3 to 4 cm. Color: Near Brown 200A. Texture: Farinose.

FOLIAGE

Leaf:

*Structure*.—Palmately compound.

*Average diameter and length*.—75 cm.

*Shape*.—Orbicular.

*Leaflets*.—Quantity: 10 per leaf Shape: Irregular linear. Length: Width: 3 cm at narrowest, 25 cm at widest. Margin: Sparse, irregular dentations. Apex: Acuminate Base: Rounded. Texture: Upper surface: Glabrous. Lower surface: Sparsely farinose. Aspect: Mainly flat. Color: Immature, Upper Side: RHS Brown 200B. Immature, Under Side: RHS Brown 200B. Mature, Upper side: RHS Yellow-Green 147A. Mature Under side: RHS Yellow-Green 146A.

*Venation*.—Type: Linear. Color upper side: RHS Yellow-Green 144A. Color under side: RHS Yellow-Green 144B.

*Petiole*.—Length: About 30 cm to 70 cm. Diameter: Approximately 6 mm. Color: Near RHS Yellow-Green 146A. Texture: Pruinose.

*Leaflet petiole* (*petiolule*).—Length: 3 cm to 10 cm. Diameter: 2.5 mm. Color: Near RHS Yellow-Green 146A. Texture: Pruinose.

FLOWERS

Flowering and fruiting not observed to date.

OTHER CHARACTERISTICS

Seeds: Not observed to date.

Fruit: Not observed to date.

Disease/pest resistance: Neither resistance nor susceptibility to normal diseases and pests of *Schefflera* have been observed.

What is claimed is:

1. A new and distinct cultivar of *Schefflera* plant named 'Mato' as herein illustrated and described.

* * * * *